United States Patent [19]

Tomita et al.

[11] Patent Number: 4,856,325
[45] Date of Patent: Aug. 15, 1989

[54] APPARATUS FOR MEASURING ADHESION

[75] Inventors: Osamu Tomita, Osaka; Kazuhiko Saiwai; Akira Kimura, both of Suita, all of Japan

[73] Assignee: Kanzaki Paper Manufacturing Co., Ltd., Tokyo, Japan

[21] Appl. No.: 237,865

[22] Filed: Aug. 29, 1988

[30] Foreign Application Priority Data

Aug. 31, 1987 [JP] Japan .................................. 62-218168
Sep. 28, 1987 [JP] Japan .................................. 62-244896

[51] Int. Cl.⁴ .............................................. G01N 19/04
[52] U.S. Cl. .................................. 73/150 A; 73/150 R; 364/550; 364/558
[58] Field of Search ................. 73/150 R, 150 A, 827, 73/829, 834, , 842; 364/550, 558, 556, 570

[56] References Cited

U.S. PATENT DOCUMENTS

| | | | |
|---|---|---|---|
| 2,762,219 | 9/1956 | Prentiss | 73/150 R |
| 2,775,888 | 1/1957 | Pickup | 73/150 R |
| 2,894,388 | 7/1959 | Cook et al. | 73/150 R |
| 3,372,583 | 3/1968 | Van Beek | 73/150 R |
| 3,412,606 | 11/1968 | Cooper et al. | 73/150 A |
| 3,524,345 | 8/1970 | Isaacson | 73/150 A |
| 3,559,475 | 2/1971 | Dillon et al. | 73/150 R |
| 4,294,111 | 10/1981 | Rutledge et al. | 73/150 R |
| 4,669,052 | 5/1987 | Bianco | 364/556 |
| 4,759,224 | 7/1988 | Charbonneau et al. | 73/862.27 |

FOREIGN PATENT DOCUMENTS 3021482 12/1981 Fed. Rep. of Germany .... 73/150 R
15192  2/1978 Japan .
62887  5/1979 Japan .

Primary Examiner—William A. Cuchlinski, Jr.
Assistant Examiner—Diego F. F. Gutierrez
Attorney, Agent, or Firm—Morgan & Finnegan

[57] ABSTRACT

Apparatus for use in the adhesion measurement of an adhesive sheet comprising a standard surface to be sticked with a main portion of the adhesive sheet, a take-up roller for pulling and taking up the free end portion of the sheet while peeling the sticked sheet portion from the standard surface by the rotation thereof, a source of driving force for rotating the take-up roller, and a torque meter interposed between the source of driving force and the take-up roller for generating torque signals corresponding to the adhesion of the adhesive sheet. The apparatus further includes: a base table extending in parallel with the standard surface; and track rolling members operatively connected to the take-up roller and mounted to a machine frame supporting the take-up roller, the torque meter and the source of driving force, and the rolling members being adapted to roll on the standard surface at the same speed with the peripheral speeed of the take-up roller.

6 Claims, 5 Drawing Sheets

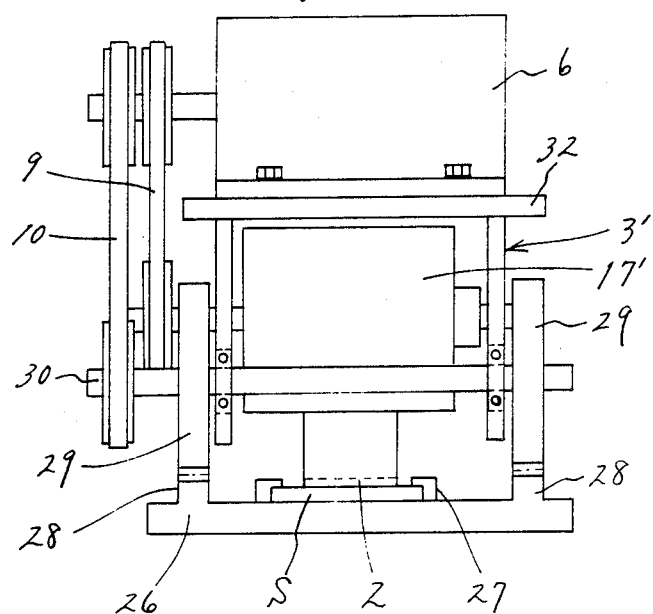
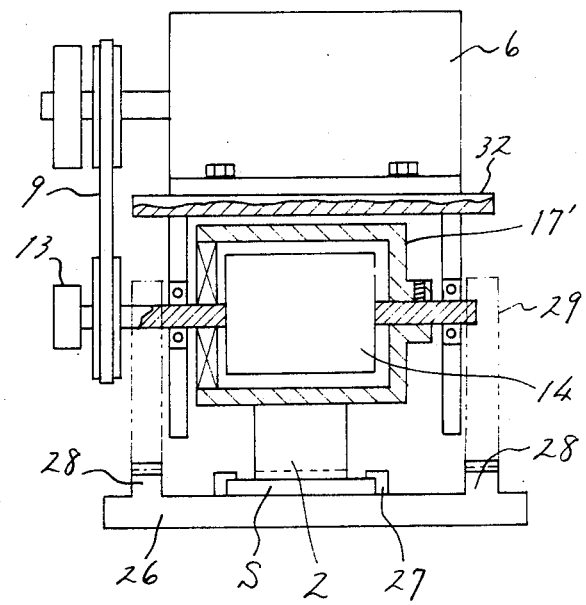

APPARATUS FOR MEASURING ADHESION

FIELD OF THE INVENTION

The present invention relates to an apparatus for measuring adhesion of adhesive sheets, such as sticker labels, adhesive tapes, adhesive papers, or the like.

BACKGROUND ART

Conventionally, there is a method of measuring adhesion of adhesive sheets, such as sticker labels, adhesive tapes, adhesive papers, or the like, which is constituted by adhering a sampled adhesive sheet to a stable surface of the substrate by securing a free end of the sampled sheet to anchor means of a tension tester, and then allowing the sampled sheet to be peeled off from the substrate so that the tester can measure the strength needed for peeling off the sampled sheet from the substrate.

Thus, a tension meter is conventionally used for measuring adhesion, but the tension meter is not inherently suited for measuring adhesion, because it is rather a stationary apparatus for rating the tensile strength of material, so that the tension matter cannot portably be transferred to the desired location. Consequently, the operator incurs much inconvenience in execution of adhesion tests in such a desired location as an adhesive-sheet manufacturing facility or in any work site where adhesive sheets are used.

Actually, there are two ways of measuring adhesive strength of adhesive sheets. The one is the 90°-peeling method which provides measurement of the strength needed for peeling off the adhesive sheet by pulling its free portion in the direction perpendicular to the adhered surface or the substrate surface. The other is the 180°-peeling method which provides measurement of the strength needed for peeling off the adhesive sheet by pulling the free portion in the direction in parallel with the adhered surface upon turning up the free portion of the adhesive sheet from the adered surface.

Generally, the tensile strength needed for peeling off the adhesive sheet from the adhered surface contains a variety of factors including the following: (1) the angle between the direction of pulling the free portion of the adhesive sheet and the sheet-adhered surface of substrate, i.e., the peeling angle itself, (2) the rate of elasticity of adhesive agent, which is variable by the peeling angle, and (3) rigidity of adhesive sheet, which is also variable by the peeling angle, i.e., elasticity and yielding stress against bending. Consequently, in order to strictly determine the peeling strength of an adhesive sheet, in principle, the tester should fully determine the peeling strength for all angles when executing peeling operations, and yet the established angle should be held constant throughout the operation for measuring angle of peeling the adhered specimen.

DISCLOSURE OF THE INVENTION

First, when executing the 90°-peeling operation for example, the tensile strength needed for peeling off the adhesive sheet from the substrate is exerted in the direction perpendicular to the substrate surface to which the adhesive sheet adheres. The position of peeling off the adhered specimen transfers itself over the adhered surface of substrate as the peeling operation proceeds, and thus, in order to correctly hold the perpendicular peeling during the operation, either the pulling device or the substrate surface having adhered specimen should be moved in accordance with the transition of the peeling position so that the pulling device can constantly remain in the position just above the sheet-peeling position at right angle.

The invention provides a carrier-type apparatus for measuring adhesion, which offers more convenience by enabling the apparatus or the pulling device to move rather than causing the surface of the adhered sheet to move.

One object of the invention is to provide a novel carrier-type apparatus for measuring adhesion of adhesive sheets, which is capable of moving the specimen-pulling mechanism of the apparatus.

To achieve the above object, the invention provides an apparatus for measuring adhesion of adhesive sheets which comprises a standard surface to be sticked with a certain longitudinal portion of the adhesive sheet as a sample to be measured, a take-up roller having an anchor means in the peripheral surface thereof to fixedly hold directly or indirectly the free end of the unsticked portion of the sheet, a source of driving force for rotating the take-up roller to tension the unsticked or peeled portion of the sheet from the peeling side of the sticked sheet portion on the standard surface and to take up the former portion thereon, and a torque meter interposed between the source of driving force and the take-up roller for generating electrical signals to indicate a roller driving torque corresponding to the tensile strength of the tensioned sheet portion which in turn corresponds to the adhesion of the adhesive sheet, characterized in that said apparatus further includes:

(a) a base table having track surface means extending in parallel with said standard surface; and (b) track rolling means operatively connected to said take-up roller and mounted to a machine frame supporting said take-up roller, said torque meter and said source of driving force, and said rolling means being adapted to roll on said standard surface at the same speed with the peripheral speed of said take-up roller when it is put on said track surface so that a constant peeling angle of the peeled sheet portion to the standard surface is maintained during the peeling operation.

Including the above type of an apparatus, generally, it is essential for all the apparatuses used for measuring adhesion to prevent the system-moving mechanism including the rolling means for rolling on table-surface and the associated driving system from adversely affecting the eventual result of the measuring operations. The adverse effect of measuring adhesion of any adhesive sheet is probably caused by provision of three shafts consisting of the input and output shafts of a torque meter, and the shaft of the takeup roller which are jointly disposed to constitute a single shaft by coupling the output shaft of torque meter to the takeup roller shaft, because these shafts can not strictly be aligned with each other. Consequently, the torque meter incurs a bending moment, even though the takeup roller is not holding the free end of the sheet specimen. Thus, the signals generated by the torque meter in a full turn of these shafts are variable even in such no load condition. Likewise, signals are also variable by the eccentricity of rollers and pulleys of a transmission system. This also eventually causes an error to be generated in the result of the adhesion measuring operation.

Another object of the invention is to provide a portable apparatus for measuring adhesion of adhesive sheets, which securely eliminates the error signals generated synchronous with the rotational angles of the roller shaft under the no-load condition.

The second object of the invention mentioned above can be achieved by either mechanically eliminating the causes of error from the adhesion measuring operation, or electrically correcting the measured value.

To mechanically solve those problems mentioned above, the invention provides a novel apparatus for measuring adhesion of adhesive sheets, which is composed of: a standard surface which allows the sheet specimen to adhesively stick thereon; a takeup roller for taking up the free extending portion of the sheet specimen while peeling it off from the standard surface; a driving source which drives the takeup roller; a torque meter which is installed between the driving source and the takeup roller; and rolling means for carrying a machine frame at least supporting the takeup roller in a specific speed exactly identical to the peripheral or the sheet-rolling up speed of the takeup roller by rolling of said means on the standard surface, characterized in that the specimen-sheet takeup roller is substantially composed of a hollow cylinder, where an end is provided with a through-hole accommodating a shaft, whereas the other end is provided with a bearing unit, and that the takeup roller allows the torque meter to coaxially be inserted into the hollow portion of the cylindrical body with the end of the input shaft or the output shaft of the torque meter being secured to the shaft-accommodating hole and the other end of the shaft or associated portion being supported by the bearing unit. This constitution allows the opposite shafts of the torque meter projecting from both sides of the takeup roller to be shared with the takeup roller itself.

This dispenses with the conventional coupling of the output shaft of the torque meter to the roller shaft used for jointly making up a single shaft. Concurrently, the above constitution eliminates the error caused by periodic distortion generated from imperfect alignment between those shafts mentioned above.

To electrically solve those problems mentioned before, the invention also provides a novel apparatus for measuring adhesion of adhesive sheets, which is composed of: a standard surface which allows the sheet specimen to adhesively stick thereon; a takeup roller which takes up the sheet specimen while peeling it off from the standard surface; a driving source which drives the takeup roller; and a torque meter which is installed between the driving source and the takeup roller, characterized in that said apparatus further includes:

(a) a position detector for detecting a rotating angular position of said takeup roller;

(b) a memory for storing no-load torque data represented by detected signals of said torque meter in corresponding with detected position signals of said position detector, in the no-load test in which said take-up roller does not take the unsticked free end position of the sheet;

(c) a data processing unit for reading out the no-load torque data from said memory, subtracting it from the load torque data represented by currently detected signals of said torque meter in angularly synchronous relation to each other and outputting the difference therebetween, in the load test in which said take-up roller takes up the sheet; and (d) an output unit for recording and indicating the subtracted torque data as the adhesion of said adhesive sheet.

By virtue of the constitution mentioned above, the apparatus causes memory to store the data which is detected when no-load is present and indicates the periodic error generated by rotation of the takeup roller, which will be included in those values given from the measurement of adhesion. On the other hand, the data processor subtracts the stored data from those data detected at the load condition, i.e., the time of pulling the specimen sheet, and thus, the periodic error caused by the rotation of the takeup roller is eventually eliminated from the measured value. As a result, precision in the measurement of adhesion is significantly improved.

A still further object of the invention is to provide a novel apparatus for measuring adhesion of adhesive sheets, which is capable of securely holding the angle of peeling off the specimen sheet at the predetermined value by moving the pulling device at a specific speed exactly matching the peripheral or the sheet-rolling up speed of the takeup roller for taking up the adhesive sheet specimen.

To achieve the above object, the invention provides the apparatus which is composed of: a standard surface which allows the specimen sheet to adhesively stick thereon; a takeup roller which takes up the specimen sheet while peeling it from the standard surface; a driving source which drives the takeup roller; a torque meter which is installed between the driving source and the takeup roller; and rolling means for carrying a machine frame at least supporting the takeup roller in a specific speed exactly identical to the peripheral speed of the takeup roller by rolling of said means on the standard surface, characterized in that said apparatus further includes:

a pair of racks which extend themselves in parallel with both sides of the standard surface; a pair of pinions which are respectively engaged with the pair of racks to constitute rotatively-moving means; and auxiliary gear means which is engaged with the pair of racks for maintaining parallel movement of the machine frame relative to these racks.

By engaging those auxiliary gears with a pair of racks, the apparatus featuring the above constitution allows the mechanical frame, i.e., the takeup roller, to precisely move itself in the direction of the transition of the sheet peeling point at a specific speed exactly identical to the peripheral speed of the takeup roller. As a result, the positional relationship between the sheet peeling point and the takeup roller remains constant. This means that the adhesive sheet specimen can always be peeled off at a constant angle while the apparatus follows up the sheet peeling operation. By adjusting the positional relationship between the sheet peeling point and the takeup roller, the apparatus can optionally establish the peeling angle in a range from 0° through 180° before entering into the peeling operation at the predetermined starting point, so that the established peeling angle can correctly be maintained all the time while executing each peeling operation.

BRIEF DESCRIPTION OF THE DRAWINGS.

FIG. 8 is a front view of the adhesion-measuring apparatus shown in FIG. 7;

FIG. 9 is a partially-exploded front view of the vertical section of the specimen-sheet takeup roller of the adhesion-measuring apparatus in accordance with the invention;

DETAILED DESCRIPTION OF PREFERRED EMBODIMENTS

Figure 1:
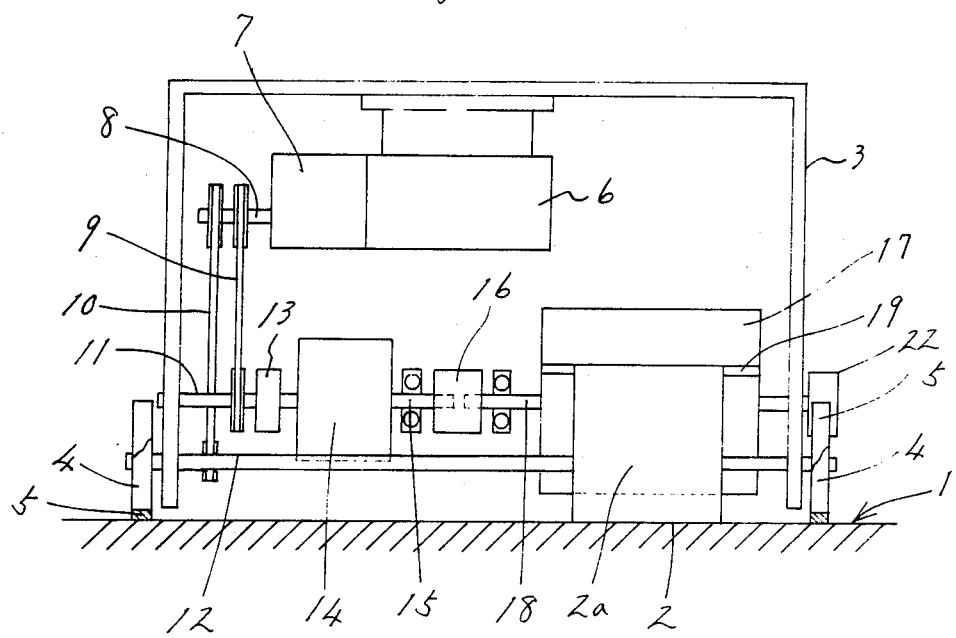
FIG. 1 is a front view of the mechanical constituents of a preferred embodiment of the adhesion-measuring apparatus in accordance with the invention.
Figure 2:
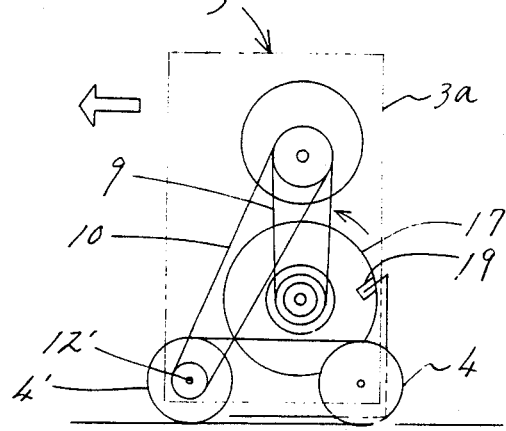
FIG. 2 is a simplified side view of the adhesion-measuring apparatus shown in FIG. 1.

FIGS. 1 and 2 show the first preferred embodiment of an adhesion-measuring apparatus in accordance with the invention. The entire constituents of the adhesion measuring apparatus are supported on the base surface 1 which function is to allow adhesion of sheet specimens thereto. The main constituents of the adhesion measuring apparatus are accommodated inside of frame 3 which is provided with a flat top structure and both-side members. Frame 3 itself is supported at a specific height on the base surface 1 by a pair of endless belts 5 installed between two pairs of transferrable pulleys 4 and 4' which are respectively supported by each own shaft at lower positions on both sides of the frame 3. Motor 6 which substantially constitutes the driving source is installed in the inner top portion of frame 3 and supports a reduction gear mechanism 7. Thus, the driving force output from motor 6 is properly reduced before it is transferred to the reduction shaft 8. Reduction shaft 8 delivers the reduced rotation force to driving shaft 11 which is installed in the lower portion of the left-side plate of frame 3 by a bearing unit as shown in FIG. 1 and also to the rear shaft 12' shown in FIG. 2 by a pair of belt means including timing belts 9 and 10. Driving shaft 11 which supports slip ring 13 is coupled to the input shaft of torque meter 14, whereas the output shaft 15 of torque meter 14 is coupled through a coupling 16 to shaft 18 of the takeup roller 17, where these shafts are provided with coaxial position. The other end of the roller shaft 18 is installed to the right-side plate of frame 3 by a bearing unit. The height of the takeup roller 17 installed to frame 3 is precisely set so that the circumferential surface of the roller can be prevented from coming into contact with the back surface of the sheet specimen adhered to the standard surface. The front pair of pulleys 4 shown in FIG. 1 are installed to idle shaft 12, whereas the rear pair of pulleys 4' are driven by shaft 12' shown in FIG. 2. In FIGS. 1 and 2, slot 19 which is drawn on the circumferential surface of the takeup roller 17 is substantially an anchor slot which first receives either the free end of the sheet specimen 2 or any lead tape secured to the free end and then anchors either of these.

Next, the method of use and functional operation of the adhesion measuring apparatus featuring the above constitution are described below. First, the operator placed the apparatus on the properly given base surface 1 which should be a perfectly horizontal plane. If the adhesion test would be executed under the provision of the JIS specification, the material and the condition of the base-surface treatment should strictly meet the specification. However, when efficiently executing comparative evaluation of adhesion in the work site, a properly selected base surface may be used. The operator first adheres a substantial portion of the adhesive sheet specimen 2 to the base surface 1, and then adheres and connects the lead tape 2a to the free end of the sheet specimen 2. Then, the operator inserts the free edge of the lead tape 2a into the slit 19 of the takeup roller 17 of the adhesion measuring apparatus, and then, firmly secures it. Next, the operator manually rotates either pair of the transfer pulleys 4 or 4' by slightly raising the apparatus itself so that the takeup roller 17 can idly rotate itself. Then, the operator places the apparatus on the base surface 1 so that the front tangent of the takeup roller 17 can be set to the position right above the peeling point P of the adhesive specimen sheet 2. In this first embodiment, the gate-shaped front surface 3a of frame 3 as shown in FIG. 2 is exactly aligned with the front tangential surface of the takeup roller 17, and thus, the operator can put the apparatus so as to position the front surface 3a of frame 3 right above the peeled portion of the sheet specimen 2. After correctly adjusting the position of the peeled portion of the sheet specimen 2 so that the peeled portion can linearly be strained at a right angle against the base surface 1, the operator then activates the motor 6.

As a result, due to the rotating force of the endless belt 5 set between the transfer-pulleys 4 and 4', while peeling off the adhesive specimen sheet 2 from the base surface 1, the apparatus retreats itself by a distance corresponding to the amount of the peeled sheet specimen 2. Slip ring 13 outputs electrical signals which indicate the rotation force needed for the takeup roller 17, and, these signals are recorded by a recorder (not shown).

Figure 3:
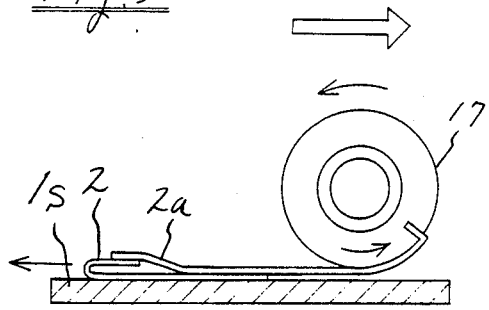
FIG. 3 is a schematic diagram of mechanical constituents for peeling off the specimen sheet at 180°.

It is noted that the test procedure mentioned above is applied to the 90°-peeling operation. However, when the 180°-peeling operation is executed, the operator has to first arrange the clearance between the circumferential surface of the takeup roller 17 and the specimen-adhered standard surface is as shown in FIG. 3 so that it doubles about the thickness of the specimen sheet 2 by applying any appropriate means, and then, disengages the endless belt 8 from the standard surface is to allow the endless belt 8 or transfer pulleys 4 and 4' to idly rotate itself or alternatively, operator may inversely drive the takeup roller 17 so that the takeup roller can move in the inverse direction at the identical speed with respect to the 90°-peeling operation at the same position.

The adhesion measuring apparatus, i.e., the sheet tensioning test machine featuring the above constitution, is wholly movable in conjunction with the rotation of the takeup roller 17 taking up the peeled-off specimen sheet 2. As a result, the adhesive sheet specimen 2 is peeled off from the base surface at a specific angle. This dispenses with any base-transferring mechanism and offers a practical advantage. Sine the transferring mechanism is installed to both sides of the takeup roller 17, this mechanism neither rolls over no presses against the sheet specimen 2 adhered to the base surface, and thus, peeling strength remains unchanged. Furthermore, since the transferring system is composed of endless belt means without using wheels or rollers, the transferring system comes into contact with substantially wide area of travelling surface. Even if the travelling surface were uneven or irregular, the travelling system either absorbs or averages it. As a result, the whole constituents of the apparatus are prevented from incurring vertical oscillation which is otherwise caused by uneven travelling surface. This in turn thoroughly eliminates noise components from the result of the measurement. Even if the travelling surface were relatively soft, unlike rollers, the endless belt means never bites into the travelling surface. Consequently, the transferring system correctly moves the apparatus by the distance corresponding to the amount of winding the sheet specimen onto the takeup roller so that the sheet specimen can be peeled off from the base surface at the predetermined angle in substantially perfect accuracy. This means that the condition of the travelling surface of the apparatus is not restrictive, thus enabling operators to execute the adhesion measuring operations anywhere by virtue of the portable constitution of the apparatus in accordance to the invention.

Furthermore, the adhesion measuring apparatus in the above preferred embodiment does not directly use the power output from the driving source for detecting the force of taking up the sheet specimen onto the takeup roller, but the apparatus is provided with torque detection means between the takeup roller and the driving shaft. As a result, neither any of the power of driving the apparatus-travelling mechanism nor the resisting force against the travelling operation can be added to the drive torque of the takeup roller to disturb the torque detecting operation, thus eventually making it possible for the apparatus in accordance with the invention to accurately detect the force of peeling off the sheet specimen from the base surface.

Figure 4:
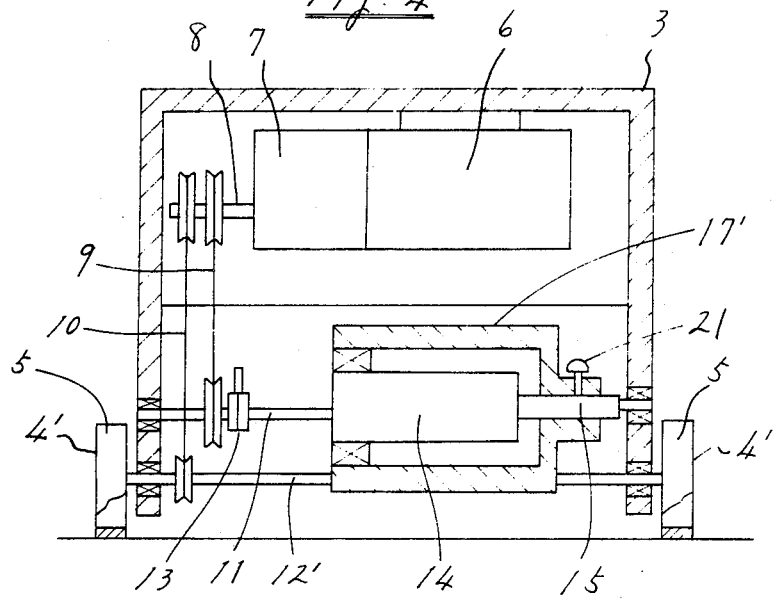
FIG. 4 is a front-sectional view of a takeup roller incorporating a torque meter and associated mechanism embodying the principle of the invention.

Another preferred embodiment of the apparatus in accordance with the invention shown in FIG. 4 is provided with a sheet takeup roller 17' which accommodates the torque meter 14 to eliminate periodic strain errors caused by the rotation of the takeup roller 17'. Those constituents which are provided with reference numerals identical to those shown in FIGS. 1 and 2 respectively have identical constitution and operational functions, and thus, description of these is deleted.

The sheet takeup roller 17' is a hollow cylinder with one end thereof (the right hand side shown in FIG. 4) having a through-hole for accommodating a shaft, whereas the other end (the left hand shown in FIG. 4) is provided with a bearing unit 20 which adjoins the torque meter 14 installed inside of the hollow chamber of the cylindrical takeup roller 17' so that the torque meter 14 shares an axis with the takeup roller 17'. The input-side portion of the torque meter 14 connected to the driving shaft 11 is rotatably supported by bearing unit 20. The output-side shaft 15 is inserted into the through-hole and secured with fastening screw 21. This allows the shaft position of torque meter 14 projecting from both sides of the cylindrical takeup roller 17' to commonly function as the shaft of this roller 17'. Consequently, the apparatus shown in FIG. 4 effectively eliminates adverse effect of the periodic strain in rotation caused by imperfect alignment between the torque meter output shaft 15 and the roller shaft 18 shown in FIG. 1. Consequently, between the one side shaft of torque meter 14 integral with the driving shaft 11 and the other side shaft integral with the takeup roller 17, the rotational distortion corresponding to the force of driving the takeup roller 17 is exerted. The torque meter 14 converts the distortion force into electrical signals, which are then output from slip ring 13 on the driving shaft 11 before these signals are delivered to the recorder (not shown).

According to the preferred embodiment of the adhesion measuring apparatus shown in FIG. 4, since the torque meter 14 is installed inside of the hollow chamber of the takeup roller 17', the apparatus is provided with the relatively narrow total width which is slightly in excess of the width of the takeup roller 17', thus materializing compact dimension of the apparatus itself and offering portable advantage as well. It is clear that all the pulleys 4 and 4' can be used for transferring rollers by controlling the rotating speed of the takeup roller 17' to be identical to that of pulley 4' in the mechanical constitution as shown in FIG. 4, thus dispensing with belt 5.

Figure 5:
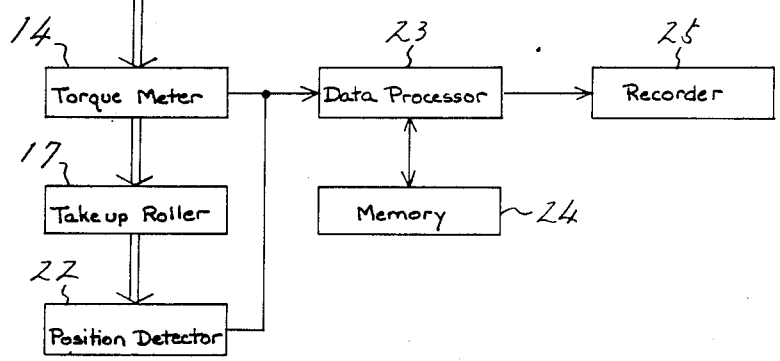
FIG. 5 is a schematic block diagram of the signal processing system which corrects an error in the adhesion measuring apparatus in accordance with the invention.

FIG. 5 is the schematic block diagram of the system circuit which electrically corrects errors caused by periodic strain in the rotation of the takeup roller 17 of the adhesion measuring apparatus shown in FIGS. 1 and 2. The way of mechanical power transmission from driving units 6 and 7 to the torque meter 14 and from the torque meter 14 to the takeup roller 17 is indicated by double arrow lines. The roller rotational position detector 22 is installed to the outside of the frame 3 in connection with the outer end of shaft 18 projecting from the takeup roller 17 as shown to the right hand of FIG. 1. The system connection is also indicated by double arrow lines shown in FIG. 5. The system circuit incorporates data processor 23, memory 24, and recorder 25 which records and indicates the output value from the data processor 23. Torque meter 14 is subjected to the distortion by the rotating force from the driving units 6 and 7 and also bythe rotating stress from the takeup roller 17. Torque meter 14 then converts the received distortion force into electrical signals, which, like the adhesion of the specimen sheet are then delivered to data processor. On the receipt of data from the roller rotating position detector 22, data processor 23 compares the signal from torque meter 14 with the rotation angle or position data output from the roller rotational position detector 22, and processes all the related data.

Figure 6:
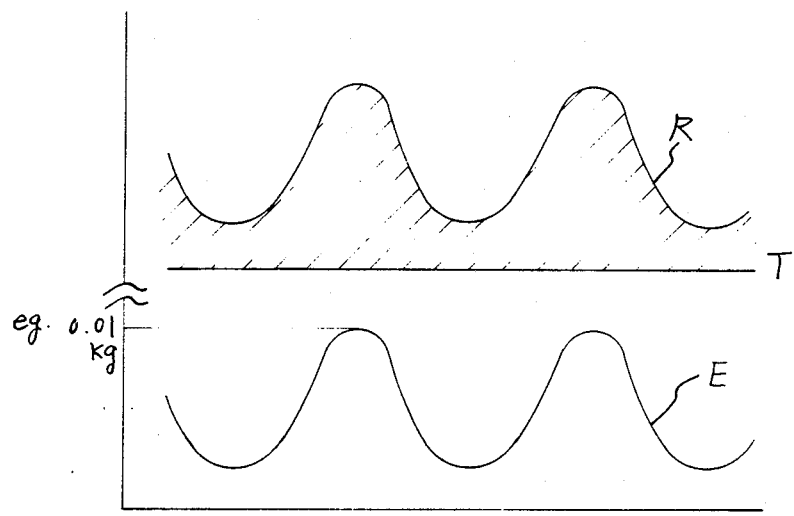
FIG. 6 is a graphical chart representing error components generated by periodic distortion of output values from the torque meter of the apparatus in accordance with the invention and various components being present when subtracting error components from the actually-measured value by means of the signal processing system shown in FIG. 5.

Next, the method of use and functional operation of the system circuit shown in FIG. 5 are described below. First, the operator idly rotates the non-loaded takeup roller 17 to detect torque corresponding to the rotational position of the takeup roller 17 by the torque meter 14, and to input the detected torque value into memory 24 together with the position detected signal from the rotational position detector 22. The no-load torque value detected by torque meter 14 indicates the periodic variation which is indicated by curve E in the lower part of FIG. 6. Next, data processor 23 receives the detected torque value R when pulling the free end of sheet specimen 2, and then, the data processor synchronously subtracts no-load signal E from the torque value R to determine the adhesion-measurement value T which is free from a periodic error component, and finally, the value T is recorded by recorder 25. Note that curve R shown in FIG. 7 representing the detected torque value also contains periodically variable components in the presence of periodic errors.

Next, referring now to FIGS. 8 and 9, another preferred embodiment of the adhesion measuring apparatus capable of strictly maintaining peeling angle is described below. Description of those constituents having reference numerals identical to those which are previously described is deleted.

Figure 7:
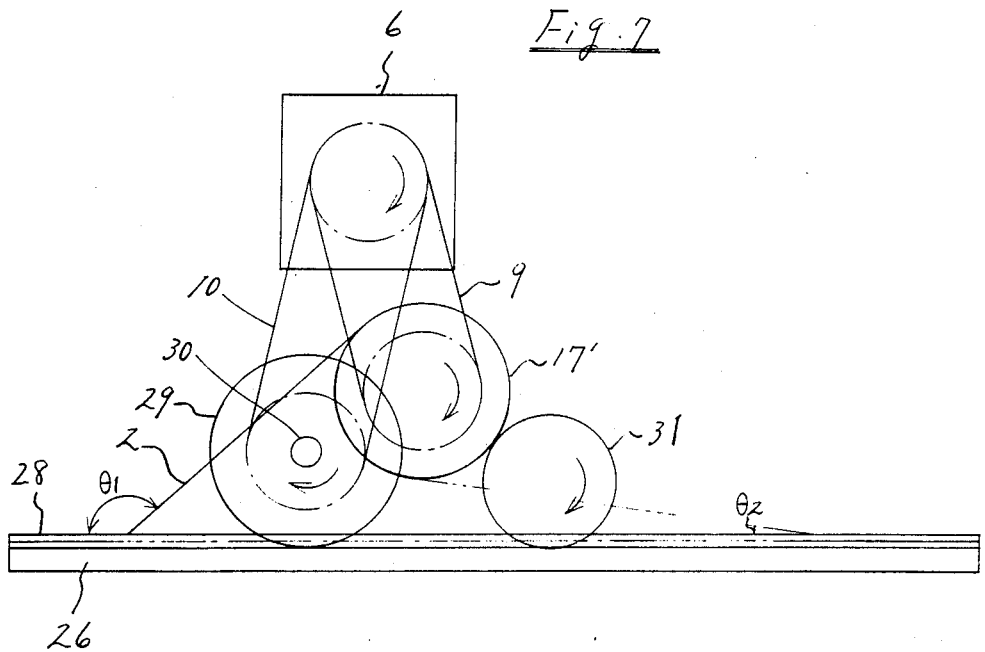
FIG. 7 is a simplified side view of the second preferred embodiment of the adhesion-measuring apparatus in accordance with the invention.

First, referring to FIGS. 7 and 8. S represents a substrate to which a specimen sheet adheres. Substrate S is firmly secured to the upper surface of trackage plate 26 by a pair of guard members 27 which hold the substrate itself. The reference numeral 28 designates a pair of racks which are installed above the trackage plate 26 in parallel with the pair of guard members 27. The reference numeral 29 designates a pair of running pinions which are respectively held on and engaged with the pair of racks 28. These pinions 29 allow the whole of the apparatus to run over the trackage plate 26. These pinions 29 are respectively secured to the output-side shaft of power-transmission belt mechanism 10. The reference numeral 31 designates a pair of auxiliary gears which, like those pinions 29, stabilize the travelling apparatus by engaging themselves with the pair of racks 28 on the trackage plate 26. FIG. 9 is the detailed diagram of the specimen-sheet takeup mechanism. Like the constitution shown in FIG. 4, the takeup roller 17' accommodates the torque meter 14 in the hollow chamber. Referring now to FIGS. 8 and 9, there is a top plate 32 of frame 3' which so functions as it securely supports the motor unit thereon.

Next, method of use of and functional operation of the apparatus shown in FIGS. 8 and 9 are described below. First, the operator places the apparatus on the base surface which is held in a substantially horizontal plane. If the adhesion measuring test should be executed based on the JIS specification, material and the condition of the base-surface treatment should strictly meet the JIS specification. However, when efficiently executing comparative evaluation of adhesion in the work site, appropriately selected base surface may be used. Then, the operator adhesively sticks the sheet specimen 2 on the upper surface of the prepared substrate S with the free end portion correctly starting with a predetermined peeling point of peel-off test. The operation then manually rotates the takeup roller 17' to the clockwise and counterclockwise directions while rolling up a free and slack portion of the sheet specimen 2 onto the takeup roller 17' which is installed above the pair of racks 28 as per the arrangement shown in FIG. 7. The operator then precisely adjusts the stretch angle of the specimen 2 to be taken onto the takeup roller 17' so that it perfectly matches the predetermined peeling angle Θ. Next, the pair of pinions 29 are respectively engaged with the pair of racks 28. Preparation is now completed by fulfilling those sequential operations mentioned above. The operator then activates the motor 6 so that it can rotate itself at the predetermined speed.

As a result, the takeup roller 17' starts to take up the specimen sheet 2 from the substrate S. Simultaneously, the pair of running pinions 29 rotate themselves to allow the frame 3 to move itself over the trackage plate 26 at a specific speed identical to the rotating speed of the takeup roller 17' for rolling up the specimen sheet 2 onto itself. Consequently, during the peeling test, the positional relationship between the position of the takeup roller 17' and the peeling point of the sheet specimen 2 remains constant. This allows the sheet specimen 2 to be precisely rolled-up onto the takeup roller 17' at the predetermined peeling angle. While the peeling operation is underway, torque meter 14 detects tension needed for peeling off the sheet specimen 2 from substrate S. The torque detected signal is externally delivered from slip ring 13 to a computer (not shown), which then stores the received data and executes arithmetic operations for the adhesion of the adhesive sheet as the result of the measurement which is eventually indicated by a display unit (not shown).

FIG. 7 is the schematic diagram representing the case in which the peeling angle $\Theta_1$ of the specimen sheet at the predetermined peeling point shown by solid line is larger than 90°. When this condition is present, the takeup roller 17' rotates in the clockwise direction, while the takeup roller 17' itself and the entire driving mechanism move to the right hand of FIG. 7 over the trackage plate 26. If the peeling angle $\Theta_1$ is to be changed into an acute angle $\Theta_2$, then the peeled portion of sheet specimen 2 indicated by solid line in FIG. 7 is displaced to the right hand of the takeup roller 17' as shown by two-dot chained line in FIG. 7, and the adhesive surface of the free or unsticked portion of the sheet 2 is faced to the substrate S, prior to the peeling test.

Figure 10:
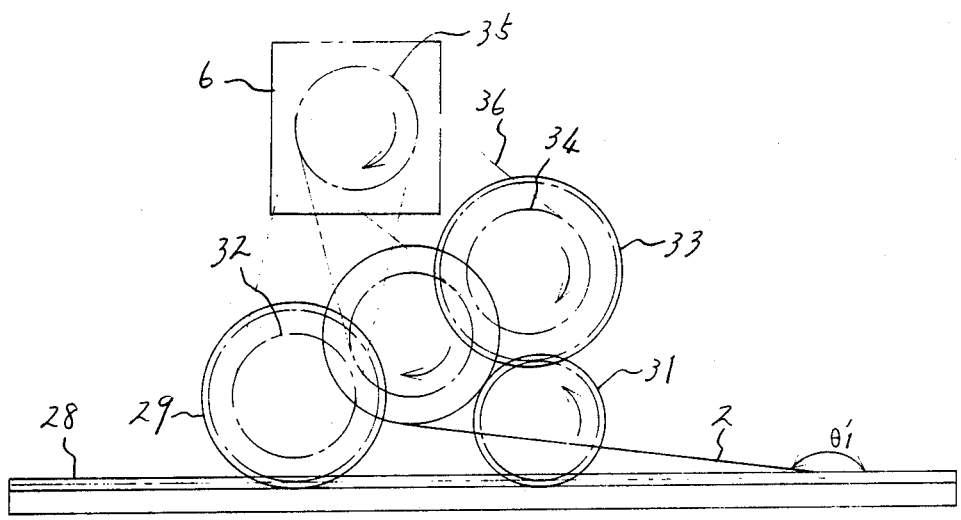
FIG. 10 is a simplified side view of the adhesion-measuring apparatus shown in FIGS. 7 through 9, which is added with reversing mechanism.

Another preferred embodiment of the adhesion measuring apparatus in accordance with the invention is described below. This apparatus executes adhesion measuring operation by applying an obtuse angle to make up the peeling angle $\Theta_1'$. As shown in FIG. 10, the operator first peels the right end of the sheet specimen 2, and then, secures it to the takeup roller 17'. Next, the operator moves the takeup roller 17' to the left of the peeling point. The operator then disengages a clutch (not shown) which is provided between the running pinion 29 and the running pulley 32. There is a reversing gear 33 to be engaged with the auxiliary gear 31. The rotating shaft of the reversing gears 33 secures a reversing pulley 34 provided with a clutch for connecting therebetween. The reversing pulley 34 and a driving pulley 35 are connected to each other by means of a timing belt 36, thus completing a mechanism for reversing the travelling direction of the sheet specimen 2. By applying the reversing mechanism mentioned above, the apparatus can effectively execute the peeling operation. Direction of the rotation of the takeup roller 17' is reversed by respectively inverting the positions of a clutch provided for the running pulley 32 and the clutch provided for reversing pulley 34. If the peeling angle is to be smaller than 90°, the operator disengages the reversing gear 33 into free-run condition by operating clutch of the reversing pulley 34, and finally drives the running pinion 29 to determine the moving direction of the peeling point relative to the rotational direction of the takeup roller in one sense. Conversely, if the peeling angle is to be larger than 90°, the operator first disengages the running pinion 29 into free-run condition by operating a clutch of the running pulley 32, and then, determines the moving direction of the peeling point relative to the rotational direction of the takeup roller in the other sense by driving the reversing gear 33. To control the operation of each of the clutchs, the associated pulley is idly coupled to the corresponding shaft. Each of the running pulley 32 and the reversing pulley 34 has a key slot at the boss portion thereof to allow insertion of a knock-pin therethrough up to the corresponding shaft. When driving either the running pulley 32 or the reversing gear 33 using only one such knock-pin, either of these should idly rotate.

All the adhesion measuring apparatuses in those preferred embodiments described above can execute operations for peeling off an adhesive sheet specimen from the base surface by precisely maintaining the pre-determined peeling angle Θ. Consequently, these apparatuses in accordance with the invention securely and correctly measure adhesion in conjunction with optional peeling angles, thus promoting capability for precisely measuring adhesion of adhesive sheets.

Figure 11:
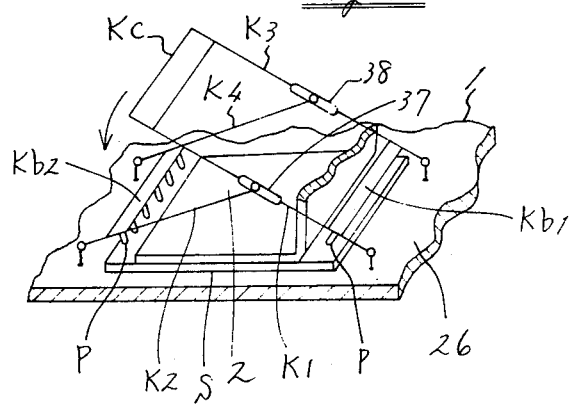
FIG. 11 is a perspective view of a modified substrate clamping mechanism used for the adhesion measuring apparatus shown in FIGS. 7 through 10.

FIG. 11 shows a system for securing the specimen-adhering substrate to the trackage plate 26 by one-shot handling operation for use with those apparatuses shown in FIGS. 7 through 9. The system shown in FIG. 11 is substantially the clamping device for holding a sheet specimen, which is composed of the following constituents. Each pair of opposite links, K1, K2 and K3, K4 being coupled to each other via hinges for K1–K2 and K3–K4 are installed to both sides of the tracking plate 26 on which a sheet specimen is placed. Of these four links, K1 and K3 which constitute a unit in parallel with each other between both sides of tracking plate 26 are respectively provided with a specific length longer than the other two links K2 and K4. Movable ends of K2 and K4 having shorter length than others are respectively connected to the other links K1 and K3 via slides 37 and 38 which are capable of freely sliding themselves in their longitudinal direction. Movable ends of the pair of longer links K1 and K3 are firmly connected to each other via coupling piece KC, whereas those portions close to the hinge-coupled ends are firmly connected to each other via bridging piece Kb2, while the bottom surface of each bridging piece is provided with pins P for securely holding the substrate.

By virtue of the constitution mentioned above, if the movable ends of longer links vertically move, then, relative to this movement, the bridging pieces Kb1 and Kb2 also vertically move themselves in a contracted range. This causes force which vertically moves the movable ends at a contracted rate to amplify and transmit itself to bridging pieces Kb1 and Kb2. As a result, pins P projecting themselves below the bottom surface of bridging pieces Kb1 and Kb2 intensely press both-side edges of substrate S below links K1 through K4 in the direction of the trackage plate 26 so that the substrate S can firmly be secured to the trackage plate 26. Such one-shot operation allows the movable ends of long links K1 and K3 to be pressed in the downward direction. Consequently, the sheet specimen can stably be fixed in position via the one-shot pressing operation.

What is claimed is:

1. Apparatus for use in the adhesion measurement of an adhesive sheet comprising a standard surface to be sticked with a certain longitudinal portion of the adhesive sheet as a sample to be measured, a take-up roller having an anchor means in the peripheral surface thereof to fixedly hold the free end of the unsticked portion of the sheet, a source of driving force for rotating the take-up roller to tension the unsticked or peeled portion of the sheet from the peeling side of the sticked sheet portion of the standard surface and to take up the former portion thereon, and a torque meter interposed between the source of driving force and the take-up roller for generating electrical signals to indicate a roller driving torque corresponding to the tensile strength of the tensioned sheet portion which in turn corresponds to the adhesion of the adhesive sheet, said apparatus further comprising:
(a) a base table having track surface means extending in parallel with said standard surface; and (b) track rolling means operatively connected to said take-up roller and mounted to a machine frame supporting said take-up roller, said torque meter and said source of driving force, and said rolling means being adapted to roll on said standard surface at the same speed with the peripheral speed of said take-up roller when it is put on said track surface so that a constant peeling angle of the peeled sheet portion to the standard surface is maintained during the peeling operation.

2. Apparatus of claim 1 wherein said track surface means is formed by reference pitch lines of a pair of parallel racks, and said track-rolling means includes a pair of pinions to engage with said pair of racks, and said apparatus further includes auxiliary gearing means being able to engage with said pair of racks to keep a constant position of said machine frame relative to said surface formed by the reference pitch lines of the racks.

3. Apparatus of claim 1 wherein said track surface means is a flat surface coplanar with said standard surface, and said track-rolling means includes a pair of endless belts for contacting said flat surface.

4. Apparatus of claim 1 wherein said takeup roller is a hollow cylinder having at one end thereof an axial through-hole and at the other thereof an opening, and said torque meter is accommodated in the hollow chamber of said cylinder, with either one of the input and output shafts of said torque meter being held by and projecting outwardly from said through-hole while the other one of the shafts projecting outwardly from said opening in rotatable relation thereto, so that said projected input and output shafts being also used as a shaft of said takeup roller.

5. Apparatus of claim 1 further including:
(a) a position detector for detecting a rotating angular position of said takeup roller;
(b) a memory for storing no-load torque data represented by detected signals of said torque meter in correspondence with detected position signals of said position detector in no-load test in which said take-up roller does not take the unsticked free end portion of the sheet;
(c) a data processing unit for reading out the no-load torque data from said memory, subtracting it from load torque data represented by currently detected signals of said torque meter in angularly synchronous relation to each other and outputting the difference therebetween in load test in which said take-up roller takes up the sheet; and
(d) an output unit for recording and indicating the subtracted torque data as the adhesion of said adhesive sheet.

6. Apparatus for use in the adhesion measurement of an adhesive sheet comprising a standard surface to be sticked with a certain longitudinal portion of the adhesive sheet as a sample to be measured, a take-up roller having an anchor means in the peripheral surface thereof to fixedly hold the free end of the unsticked portion of the sheet, a source of driving force for rotating the take-up roller to tension the unsticked or peeled portion of the sheet from the peeling side of the sticked sheet portion on the standard surface and to take up the former portion thereon, and a torque meter interposed between the surface of driving force and the take-up roller for generating electrical signals to indicate a roller driving torque corresponding to the tensile strength of the tensioned sheet portion which in turn corresponds to the adhesion of the adhesive sheet, said apparatus further comprising:

(a) a position detector for detecting a rotating angular position of said takeup roller;

(b) a memory for storing no-load torque data represented by detected signals of said torque meter in correspondence with detected position signals of said position detector in no-load test in which said take-up roller does not take the unsticked free end portion of the sheet;

(c) a data processing unit for reading out the no-load torque data from said memory, subtracting it from load torque data represented by currently detected signals of said torque meter in angularly synchronous relation to each other and outputting the difference therebetween in load tests in which said take-up roller takes up the sheet; and (d) an output unit for recording and indicating the subtracted torque data as the adhesion of said adhesive sheet.

* * * * *